United States Patent [19]

Homan

[11] 4,212,886

[45] Jul. 15, 1980

[54] STABILIZED BENACTYZINE HYDROCHLORIDE

[75] Inventor: Gerlof Homan, St. Louis, Mo.

[73] Assignee: Survival Technology, Inc., Bethesda, Md.

[21] Appl. No.: 956,987

[22] Filed: Nov. 1, 1978

[51] Int. Cl.² .......................................... A61K 31/235
[52] U.S. Cl. ................................................... 424/308
[58] Field of Search ......................................... 424/308

[56] References Cited

U.S. PATENT DOCUMENTS

| | | | |
|---|---|---|---|
| 2,784,141 | 3/1957 | Jacobsen | 424/308 |
| 3,746,743 | 7/1973 | Mehta et al. | 424/308 |
| 4,007,282 | 2/1977 | Mauz et al. | 424/308 |

OTHER PUBLICATIONS

The Pharmacological Basis of Therapeutics–p. 977 (1966).
The Merck Index, 9th ed. (1960)–p. 1035.

*Primary Examiner*—Douglas W. Robinson
*Attorney, Agent, or Firm*—Cushman, Darby & Cushman

[57] ABSTRACT

Benactyzine hydrochloride is stabilized in a mixture of propylene glycol and water. Preferably a small amount of ethanol is present.

10 Claims, No Drawings

STABILIZED BENACTYZINE HYDROCHLORIDE

BACKGROUND OF THE INVENTION

Benactyzine hydrochloride is a drug having utility, for example as an anticholinergic and ataraxic. It is soluble in water. However, the shelf life of such solutions is not as long as is necessary for some uses, resulting in the need for relatively frequent replacement of the solutions. This is increasingly true when storage is not in the refrigerator but instead is at normal room temperature (about 20° C.) or more elevated temperatures as occurs, for example, in the summer or in hot climates. Due to the problems mentioned above there is no injectable solution of the drug on the market.

SUMMARY OF THE INVENTION

Accordingly, it is the purpose of the invention to develop a solution of benactyzine hydrochloride which has a shelf life which has significantly increased duration and which is less dependent upon storage temperatures.

It has been found experimentally that the decomposition of benactyzine hydrochloride is because of a proton induced hydrolysis. Furthermore, it has been found that the reaction rate (i.e. decomposition rate) is related to the pH of the aqueous solution, i.e. an increase in hydrogen ion concentration decreases the rate of decomposition.

In order to suppress the hydrolysis of benactyzine into benzilic acid and diethylaminoethanol, ideally a non-ionic solvent had to be selected. The solvent should desirably meet the following requirements:
1. It is non-toxic;
2. It is stable;
3. Decomposition products of the solvent are non-toxic;
4. It is non-ionic;
5. It is water soluble in order to increase the absorption speed when the benactyzine hydrochloride is injected into the body;
6. It is compatible with the product and, if an injection is used, with the injector component and also creates no technical problems.

It has been found that propylene glycol meets all of the requirements set forth above. However, the use of pure propylene glycol as a diluent for the drug creates the following problems:
  (a) dehydration of the benactyzine;
  (b) possible reesterification;
  (c) too high viscosity for use in an injector.

It has been found that these problems can be overcome by using a mixture of propylene glycol and water in the range of 30 to 70% of propylene glycol by volume and the balance water. In order to decrease the viscosity of the solution it has been found advantageous to add ethanol in an amount of 5 to 15% by volume. The reduction in viscosity renders it easier to inject the solution. However, the alcohol is not needed for stability purposes and can be omitted. When alcohol is present the amount of water can be as low as 15% by volume. Preferably the propylene glycol is 40 to 70% by volume.

The presently preferred solvent mixture is 50% propylene glycol, 40% water and 10% ethanol by volume.

It has been found that the rate of hydrolysis of benactyzine hydrochloride is reduced significantly in the mixture of propylene glycol and water compound to the hydrolysis in an equally concentrated solution in water. As a result the shelf life expectation of the solution of drug is significantly increased as compared to an equal solution in water.

The solvent mixture of the invention can be employed with any concentration of benactyzine hydrochloride which does not exceed the solubility limit. Generally the concentration is 1.03 to 4.14 mg of benactyzine hydrochloride per ml of solution, preferably 2.07 mg per ml of solution.

The decomposition reaction rate of benactyzine hydrochloride is related to the concentration of the drug. For any specific concentration, however, the stability of the benactyzine hydrochloride in the mixture of propylene glycol and water of the invention is better than the stability in water alone.

The composition of the invention can comprise, consist essentially of or consist of the materials set forth. The solvent can comprise, consist essentially of or consist of the materials set forth.

DESCRIPTION OF THE PREFERRED EMBODIMENT 4.14 mg of benactyzine hydrochloride was dissolved in 2 ml of a mixture consisting of 50% propylene glycol, 40% water and 10% ethanol by volume.

What is claimed is:

1. A pharmaceutical composition comprising a therapeutically effective amount of benactyzine hydrochloride dissolved in a solvent mixture consisting of propylene glycol and water, the propylene glycol being present in an amount of 30 to 50% by volume and sufficient to increase the stability of the benactyzine hydrochloride over that in water alone and the water being present in an amount of 70 to 50% by volume and sufficient to prevent dehydration of the benactyzine hydrochloride.

2. A pharmaceutical composition consisting essentially of a therapeutically effective amount of benactyzine hydrochloride dissolved in a solvent mixture consisting of 50% propylene glycol, 40% water and 10% ethanol by volume.

3. A composition according to claim 2 wherein there is present 2.07 mg of benactyzine hydrochloride per ml.

4. A composition according to claim 1 wherein the propylene glycol is 30% by volume of the total solvent.

5. A composition according to claim 1 which contains 1.03 to 4.14 mg of benactyzine hydrochloride per ml.

6. A composition according to claim 1 containing 2.07 mg of benactyzine hydrochloride per ml.

7. A composition according to claim 1 wherein the solvent mixture consists of 50% propylene glycol and 50% water by volume.

8. A composition according to claim 1 wherein the solvent mixture consists of 40% propylene glycol and 60% water.

9. A composition according to claim 8 containing 1.03 to 4.14 mg of benactyzine hydrochloride per ml.

10. A composition according to claim 9 containing 2.07 mg of benactyzine hydrochloride per ml.

* * * * *